United States Patent [19]

Spielberger et al.

[11] 4,065,492
[45] Dec. 27, 1977

[54] PROCESS FOR PREPARING AMINONAPHTHALENE DERIVATIVES IN A TITANIUM OR TITANIUM ALLOY REACTOR

[75] Inventors: Georg Spielberger, Leverkusen; Hermann Wunderlich, Odenthal-Hahnenberg; Günther Klag, Leverkusen; Marko Zlokarnik, Cologne, all of Germany

[73] Assignee: Bayer Aktiengesellschaft, Leverkusen, Germany

[21] Appl. No.: 698,563

[22] Filed: June 22, 1976

[30] Foreign Application Priority Data

July 12, 1975 Germany .................... 2531281

[51] Int. Cl.$^2$ ............................. C07C 85/06
[52] U.S. Cl. ................... 260/508; 23/252 A; 75/175.5; 260/509; 260/510; 260/518 R; 260/518 A; 260/519; 260/571; 260/574; 260/576; 260/577; 260/581
[58] Field of Search ............ 260/581, 577, 576, 508, 260/518 R; 75/175.5; 23/252 A

[56] References Cited

FOREIGN PATENT DOCUMENTS 631,882  1/1962  Italy ................... 260/585 A

OTHER PUBLICATIONS

Cotton et al., "The Chemical Engineer", No. 226, pp. CE89–CE95, (1969).
Glukhova et al., "Chemical Abstracts", vol. 67, Ab. No. 49827x, (1967).
Feige et al., "Chemical Engineering Progress", vol. 66, No. 10, pp. 53–56, (1970).
Cotton, "Chemical Engineering Progress", vol. 66, No. 10, pp. 57–62, (1970).
Tavadze et al., "Chemical Abstracts", vol. 81, Ab. No. 15914x, (1974).
Bomberger et al., "Chemical Abstracts", vol. 72, Ab. No. 5727p, (1970).

*Primary Examiner*—Daniel E. Wyman
*Assistant Examiner*—John J. Doll
*Attorney, Agent, or Firm*—Burgess, Dinklage & Sprung

[57] ABSTRACT

Aminonaphthalene derivatives are prepared by reacting the corresponding naphthol derivative with ammonia or amines in the presence of bisulfites. The reaction is carried out in a continuous procedure in reaction apparatus which consists wholly or partly of titanium or a titanium alloy, carbon largely excluded. Suitable alloys are titanium/palladium, titanium/nickel or titanium/molybdenum.

9 Claims, No Drawings

PROCESS FOR PREPARING AMINONAPHTHALENE DERIVATIVES IN A TITANIUM OR TITANIUM ALLOY REACTOR

BACKGROUND

This invention relates to a continuous process for the preparation of aminonaphthalene derivatives.

It is known to prepare derivatives of aminonaphthalenes from the corresponding derivatives of a naphthol and ammonia or amines in an aqueous medium in the presence of a bisulphite according to the so-called Bucherer reaction (Org. Reactions 1, 105 (1942), and Angew. Chem. 79, 329 (1967)).

The Bucherer reaction is generally carried out discontinuously under autogenous pressure at elevated temperature in a closed stirred kettle (Ullmanns Encyclopedia of Industrial Chemistry 7, 995 (1974).

When carrying out the discontinuous process it is a disadvantage that, when the reaction is ended, large amounts of gas and steam, which generally are contaminated with traces of animonaphthalene derivatives, are liberated in a short time. Since these traces of aminonaphthalene derivatives have to be separated off for ecological reasons, an expensive absorption system is necessary. With the continuous procedure, such problems are avoided since the amino-naphthalene derivatives which are not separated off can be recycled into the process.

Stainless steels of the VA type and cast steel are known as materials for apparatus in which the Bucherer reaction can be carried out (Ullmanns Encyclopedia of Industrial Chemistry, 4th edition, volume 7, 396 (1974). These materials are sufficiently resistant to corrosion for carrying out the discontinuous process. However, carrying out the continuous process in apparatus made of the said materials leads to stress corrosion cracking and pitting. The high susceptibility of the known materials to corrosion prevents the continuous process being carried out.

SUMMARY

A process for the preparation of aminonaphthalene derivatives by reacting the corresponding naphthol derivatives with ammonia or amines in the presence of bisulphites has now been found, in which the reaction is carried out, by a continuous procedure, in reaction apparatus which consists wholly or partly of titanium or a titanium alloy, elementary carbon being largely excluded.

DESCRIPTION

Commercially available titanium metal can be employed for the process according to the invention. The commercially available titanium metal can either be pure or also contain impurities. Possible impurities are in the main traces of iron, carbon, nitrogen, oxygen and hydrogen. The proportion of impurities alongside titanium metal is generally 0 to 0.5 percent by weight. A titanium which contains 99.848 percent by weight of titanium, 0.03 percent by weight of iron, 0.01 percent by weight of carbon, 0.01 percent by weight of nitrogen, 0.1 percent by weight of oxygen and 0.002 percent by weight of hydrogen is preferentially employed as the material.

Titanium alloys according to the process of the invention are understood as materials which consist mainly of titanium.

Titanium alloys for the process according to the invention can contain, for example, palladium, nickel, molybdenum, aluminium, magnesium, beryllium, tin, chromium and iron, preferably palladium, nickel and molybdenum, as constituents of the alloy. Titanium alloys of a commercially available quality which contain, as the impurity, in the main iron, nickel, molybdenum, carbon, nitrogen, oxygen and hydrogen, can be employed for the process according to the invention. Preferably, titanium/palladium alloys for the process according to the invention contain 99.0 to 99.5% by weight of titanium and 0.05 to 0.2% by weight of palladium, titanium/nickel alloys contain 97.0 to 99.5% by weight of titanium and 0.5 to 3.0% by weight of nickel and titanium/molybdenum alloys contain 50.0 to 80.0% by weight of titanium and 20.0 to 50.0% by weight of molybdenum. A titanium/palladium alloy which contains 99.36 percent by weight of titanium, 0.2 percent by weight of palladium, 0.2 percent by weight of iron, 0.08 percent by weight of carbon, 0.05 percent by weight of nitrogen and 0.01 percent by weight of hydrogen is preferentially employed.

According to the process of the invention, elementary carbon is substantially excluded from all parts of the reaction apparatus in contact with the reaction materials, such as, for example, the titanium metal or the titanium alloy, the packing constituents of the shaft glands and stuffing boxes, and from the lubricants.

Graphite and carbon black may be mentioned in particular as elementary carbon.

Elementary carbon is considered to be substantially excluded, for example, when the carbon content in the system used is less than 0.1 percent by weight, preferably less than 0.08 percent by weight.

Substantial exclusion of carbon from the packing constituents of the shaft glands, the stuffing boxes and the lubricants is achieved by using materials which do not contain carbon. Such materials are, for example, Teflon, asbestos and carbon-free greases and oils.

Starting materials which can be used for the continuous preparation of aminonaphthalene derivatives by reacting the corresponding naphthol derivatives with ammonia and amines in the presence of bisulphite ions according to Bucherer are all the naphthol derivatives which are accessible to this reaction.

Preferred naphthol derivatives for the process according to the invention are naphthalenesulphonic acids and/or naphthalenecarboxylic acids of the general formula

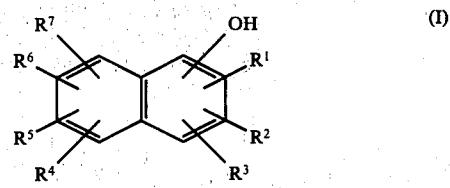

(I)

wherein
$R^1$ represents hydrogen, the hydroxyl, amino, carboxylic acid or sulphonic acid group, chlorine or the methyl or ethyl radical and
$R^2$ to $R^7$ are identical or different and represent hydrogen, the amino, carboxylic acid or sulphonic acid group, chlorine or the methyl or ethyl radical and the number of carboxylic acid or sulphonic acid groups is at most 3.

Preferably, the compounds of the formula I are employed in the form of their alkali metal salts or ammonium salts. Sodium, potassium or lithium salts, preferably sodium salts, may be mentioned as examples of an alkali metal salt.

Preferred naphthol derivatives for the process according to the invention are α-naphthol and β-naphthol, 2-hydroxynaphthalene-1-sulphonic acid, 2-hydroxynaphthalene-6-sulphonic acid, 2-hydroxynaphthalene-8-sulphonic acid, 2-hydroxynaphthalene-3,6-disulphonic acid and 2-hydroxynaphthalene-6,8-disulphonic acid.

All the amines which can be employed for the Bucherer reaction can be used as amines. Preferred amines for the process according to the invention are ammonia, methylamine and ethylamine, aniline and optionally substituted aniline.

Bisulphites which may be mentioned are the alkali metal bisulphites, but preferably ammonium bisulphites and sodium bisulphites.

In general, all the aminonaphthalene derivatives which are obtainable according to the Bucherer process can be obtained according to the process of the invention. Preferred aminonaphthalene derivatives which can be prepared according to the process of the invention are compounds of the formula

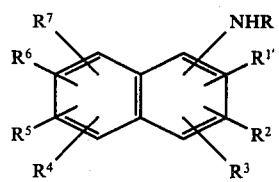

wherein
R represents hydrogen, methyl, ethyl or optionally substituted phenyl,
$R^{1'}$ represents hydrogen, the —NHR group, the amino, carboxylic acid or sulphonic acid group, chlorine or the methyl or ethyl radical, and
$R^2$ to $R^7$ have the abovementioned meaning.

For example, 1-methylaminonaphthalene, 2-methylaminonaphthalene, 1-ethylaminonaphthalene, 2-ethylaminonaphthalene, 2-amino-naphthalene-1-sulphonic acid, 2-aminonaphthalene-6-sulphonic acid, 2-aminonaphthalene-8-sulphonic acid, 2-aminonaphthalene-3,6-disulphonic acid and 2-aminonaphthalene-6,8-disulphonic acid can be prepared according to the process of the invention.

The process according to the invention can be carried out particularly advantageously in an apparatus which consists of at least 5, preferably 10 to 20, reaction chambers, each individual chamber being provided with a stirrer. In general, the number of chambers depends on the desired degree of conversion, the back-mixing between the chambers, the rate of reaction, the necessary residence time and the throughput and depends indirectly on the ratio of the reactants (see Ullmann 1, 266 - 71 (1972) and Ullmann 3, 342-56 (1972)). Since it is known that a certain ratio of the height to the diameter of the chambers of a reactor is the most appropriate and that the manufacture of a multi-stage reactor is uneconomically expensive, the number of chambers will generally be restricted to less than 25. The design of the apparatus for the reactor kettle cascade, a horizontal or vertical multi-chamber reactor or a multi-stage loop reactor is in itself known. (Ullmann 1, 266-71, (1972) and Ullmann 3, 342-56 (1972)).

When carrying out the process according to the invention the temperature is generally kept in the same range as is customary for carrying out the Bucherer reaction discontinuously. In general, the reaction is carried out in a temperature range of 60° to 220° C, preferably at 100° to 180° C.

In general, the process is carried out under a pressure which is equal to or higher than the autogenous vapour pressure of the reaction mixture. When ammonia, methylamine or ethylamine is used, the pressure range from 1 to 30, especially 3 to 20 bars is preferred, whilst when aniline is used as the starting compound the pressure range from 1 to 10 bars, especially 1 to 5 bars, is particularly advantageous.

It is also possible for the temperature and the pressure to display a gradient along the length of the reaction path. Thus, for example, it can be appropriate to allow the temperature to rise continuously or step-wise from the inlet to the outlet of the apparatus; it can also be appropriate to allow the pressure to fall continuously or step-wise along the length of the apparatus from the inlet to the outlet.

Generally all the parts of the apparatus which are subject to chemical attack, where they are exposed simultaneously to elevated pressure and/or elevated temperature, are manufactured from the material according to the invention, that is to say titanium or a titanium alloy. Essentially, these are parts which can corrode under the influence of the starting materials and auxiliaries, of the reaction mixture and of the reaction products, such as, for example, inner surfaces of the reactor, valves, pipes, pumps, stirrer shafts and stirrer blades.

Other materials which are inert under the conditions are also possible for the parts of the apparatus which are subject to less severe physical stress, for example the sheet metal dividers between the individual chambers. Suitable materials are, for example, plastics reinforced by glass fibres. However, the use of these inert materials generally offers no technical advantage over the design of these parts of the apparatus in titanium or a titanium alloy.

Usually, the process according to the invention is carried out as follows:

The naphthol derivative selected as the starting compound is introduced, as an aqueous solution and/or suspension, into the first chamber of a multi-chamber reactor made of titanium or a titanium alloy, the individual chambers of which reactor can be heated separately. At the same time, all or part of the liquid ammonia or the amine and/or aqueous solutions of ammonia or the amine are introduced into the same chamber. Depending on the naphthol derivative selected, and when only part of the liquid ammonia or amine selected is fed into the first chamber, the remaining parts are fed into one or more subsequent chambers in one or more side-streams. The aqueous solution containing the bisulphite is also fed into the first chamber. It is also possible for all the starting components to be introduced together, premixed upstream of the first chamber.

The temperatures of the individual chambers can be set to be equal or different, depending, for example, on the starting compounds selected, the rate of reaction and the throughput. When liquid ammonia is used as the amine component, and especially when the liquid ammonia or liquid amine is introduced into subsequent reaction chambers, it can be appropriate to keep the individual chambers at different temperatures, since the heat requirement for heating of the liquid ammonia or amine is different in the different chambers.

In general, it is appropriate to carry out the reaction as completely as possible in the liquid phase. This is achieved when the pressure selected is equal to or higher than the vapour pressure of the reaction mixture. Advantageously, the reaction pressure is adjusted with the aid of a let-down valve at the end of the reactor.

The reaction product can be worked up batch-wise or continuously. For example, the reaction product can be allowed to run continuously into a heated kettle, whilst stirring, and, by simultaneously adding milk of lime which contains 20 to 30 percent by weight of calcium hydroxide, both the dissolved ammonia can be expelled as a gas and the bisulphite ions can be precipitated as calcium sulphite. Subsequently, the resulting suspension is filtered, for example through a suction filter or a rotary filter, and the sparingly soluble aminonaphthalene derivative is then precipitated with acids, for example aqueous sulphuric acid. An excess of 10 to 80% strength aqueous sulphuric acid is preferably used in order to precipitate the aminonaphthalene derivative.

Another possibility for working up consists in adding sodium hydroxide solution in a stoichiometric amount or in excess of the stoichiometric amount to the reaction mixture. After the ammonia or amine, employed in excess, present in the reaction mixture has been driven off as a gas by warming, the aminonaphthalene derivative or the sparingly soluble alkali metal salt can be separated off from the solution containing the bisulphite by filtering or can be precipitated from the aqueous alkaline solution by adding acid or by introducing the solution into an acid.

The use, according to the invention, of titanium or titanium-containing alloys and the exclusion of carbon from the Bucherer reaction makes it possible, in an advantageous manner, to carry out the process continuously. An advantage which may be mentioned of carrying out the Bucherer reaction continuously is that smaller apparatus can be used both for carrying out the reaction itself, which, as is known, requires long reaction times, and for working up the reaction mixture than in the case of the discontinuous process. The effect of the continuous utilisation of the apparatus required for working up the reaction mixture is thus a saving in costs.

It is also an advantage that, when the Bucherer reaction is carried out continuously, using, according to the invention, titanium or titanium-containing alloys and excluding carbon, corrosion is substantially less than when the materials known for the Bucherer reaction are used.

The aminonaphthalene derivatives which can be prepared according to the Bucherer reaction are intermediate products for dyestuffs.

EXAMPLES

A vertical 8 m$^3$ reactor made of titanium-clad steel is used in Examples 1 to 5. The titanium cladding has the following composition: 99.848 percent by weight of titanium, 0.01 percent by weight of carbon, 0.01 percent by weight of nitrogen, 0.03 percent by weight of iron, 0.1 percent by weight of oxygen and 0.002 percent by weight of hydrogen.

The reactor is subdivided into ten chambers by means of baffles. A continuous stirrer shaft, which carries an agitator grid in each chamber, is passed through the baffles. The baffles and the agitator grids are manufactured from titanium of the abovementioned composition. The necessary gaskets consist of Teflon and the packing for the stuffing boxes consists of asbestos string and/or fluorinated polyethylene.

The design of the heating for the reactor is such that the individual reaction chambers can be kept at the same temperature or at different temperatures, as desired. The reactor is also provided with feed lines through which the starting compound can be fed in both at the base of the lowest chamber and, as desired, into individual other chambers.

The reaction product is taken off in one stream in a let-down valve at the upper end of the reactor. The pressure is adjusted with the aid of the let-down valve. The pressure is so selected that the reactor is filled as completely as possible with the reaction mixture, which is liquid at this pressure, during the continuous process.

EXAMPLE 1

970 l of an aqueous solution which is warmed to 95° C and which contains, per liter, 200 g (0.81 mole) of the sodium salt of 2-hydroxynaphthalene-6-sulphonic acid and 26.3 g (0.265 mol) of ammonium bisulphite, and 74 l (2.66 k mols) of liquid ammonia are metered, per hour, into the lowest chamber of the reactor, all the chambers of which are heated to 160° C. The reaction mixture is taken off continuously at the top of the reactor at a pressure of 14 to 16 bars.

4,469 l, at a time, of the reaction mixture thus obtained are fed into a receiver containing 137 l (2.61 k mols) of 50% strength sodium hydroxide solution. The excess ammonia is distilled off and the hot solution is treated with active charcoal. After filtering off the insoluble residues, the solution is cooled and the sodium salt of 2-aminonaphthalene-6-sulphonic acid, which has precipitated, is isolated.

71.2 kg (which corresponds to 97% of theory) of the sodium salt of 2-aminonaphthalene-6-sulphonic acid are obtained per hour.

The wear of the titanium surfaces wetted by the reaction mixture is 0.1 mm after a running time of 1 year; when elementary carbon is largely excluded, the wear is < 0.01 mm.

EXAMPLE 2

The procedure is as in Example 1 but 495 l (0.4 k mol) of 2-hydroxynaphthalene-6-sulphonic acid and 98 l of liquid ammonia are introduced per hour.

After working up analogously to Example 1, 96 kg (which corresponds to 98% of theory) of 2-aminonaphthalene-6-sulphonic acid of 96% purity are obtained per hour.

The wear of the titanium surfaces wetted by the reaction mixture is 0.1 mm after a running time of 1 year; when elementary carbon is largely excluded, the wear is < 0.01 mm.

EXAMPLE 3

A suspension of 285 kg (0.75 k mol) of the dipotassium salt of 2-hydroxy-naphthalene-6,8-disulphonic acid in an aqueous ammonia solution, which contains 245 kg of water and 27 kg (1.59 k mol) of ammonia, 23 l (0.18 k mol) of an aqueous ammonium bisulphite solution containing 500 g of SO$_2$/liter and 35 l (1.26 k mols) of liquid ammonia are introduced simultaneously, per hour, into the reactor described above. The reaction temperature in all the chambers is kept at about 180° to 185° C. The pressure is adjusted to 28 to 30 bars by means of the let-down valve at the end of the reactor.

The reaction mixture is worked up continuously by adding 30 l (0.57 k mol) of a 50 percent strength by weight aqueous sodium hydroxide solution per hour. The excess ammonia is distilled off at 120° C through a column. After cooling, the di-sodium salt of 2-aminonaphthalene-6,8-disulphonic acid precipitates out and is separated off continuously.

255 g (which corresponds to 98% of theory) of the disodium salt of 2-aminonaphthalene-6,8-disulphonic acid in a purity of about 99% are obtained per hour.

The wear of the titanium surfaces wetted by the reaction mixture is 0.05 mm after a running time of 1 year; when elementary carbon is largely excluded the wear is < 0.01 mm.

EXAMPLE 4

In the reactor described above, 360 l of an aqueous solution of 120 kg (0.49 k mol) of the sodium salt of 2-hydroxynaphthalene-1-sulphonic acid and 18 kg (1.06 k mols) of ammonia, 60 l of an ammonium bisulphite solution (consisting of 500 g (0.47 k mol) of $SO_2$ per liter and 58 l (2.08 k mols) of liquid ammonia are fed per hour, in three separate streams at the same time, into the lowest chamber of the reactor. The entire reactor is kept at a temperature of about 135° to 145° C. The reaction mixture is taken off continuously at the top of the reactor at a pressure between 13 and 15 bars. The aqueous reaction solution is fed continuously into a cyclone flash vaporiser and let down. The solution loses about 1 kg of ammonia per hour in the form of a 16 to 25% strength ammonia/steam mixture. After cooling the reaction mixture to 50° to 60° C. 70 to 105 l (0.5 to 0.75 k mol) of 50% strength sulphuric acid are added and the resulting sulphur dioxide is driven off by passing air through the mixture. After further cooling, 2-amino-naphthalene-1-sulphonic acid precipitates out.

106 kg (which corresponds to 97% of theory) of 2-amino-naphthalene-1-sulphonic acid in a purity of 99% are obtained per hour.

The wear of the titanium surfaces wetted by the reaction mixture is 0.1 mm after a running time of 1 year; when elementary carbon is largely excluded the wear is < 0.01 mm.

EXAMPLE 5

Using the same procedure as in Example 4, 50% of the amount of liquid ammonia used are pumped into the first chamber, 30% are pumped into the third chamber and 20% are pumped into the sixth chamber. At the same time, 500 l of an aqueous solution of 167 kg (0.68 k mol) of the sodium salt of 2-hydroxynaphthalene-1-sulphonic acid and 25 kg (147 k mols) of ammonia are introduced into the first chamber per hour. The temperature is kept at about 110° to 115° C in the lower three chambers, at about 115° to 120° C in the fourth and fifth chambers and at 120° to 125° C in the remaining five chambers. The reaction pressure is 5 to 6 bars in all the chambers.

Working up is carried out in the manner described in Example 4. 147 kg (which corresponds to 97% of theory) of 2-aminonaphthalene-1-sulphonic acid in a purity of 99% are obtained per hour.

The wear of the titanium surfaces wetted by the reaction mixture is 0.1 mm after a running time of 1 year; when elementary carbon is largely excluded the wear is < 0.01 mm.

EXAMPLE 6

9.7 l of an aqueous solution which is warmed to 95° C and which contains, per liter, 200 g (0.81 mol) of the sodium salt of 2-hydroxynaphthalene-6-sulphonic acid and 26.3 g (0.265 mol) of ammonium bisulphite, and 0.74 l (26.6 mols) of liquid ammonia are metered, per hour, into the first chamber of a 10-stage kettle cascade, all the stages of which are heated to 160° C. The reaction mixture is taken off continuously from the 10th chamber at a pressure of 14 to 16 bars.

44.7 l at a time of the reaction mixture thus obtained are fed into a receiver containing 1.37 l (26.1 mols) of 50% strength sodium hydroxide solution. The excess ammonia is distilled off and the hot solution is treated with active charcoal. After filtering off the insoluble residues, the solution is cooled and the sodium salt of 2-aminonaphthalene-6-sulphonic acid, which had precipitated, is isolated.

0.71 kg (which corresponds to 97% of theory) of the sodium salt of 2-aminonaphthalene-6-sulphonic acid are obtained per hour.

The wear of the titanium cladding is 0.08 mm after a running time of 1 year; when elementary carbon is largely excluded the wear is < 0.01 mm.

What is claimed is:

1. In a process for preparing aminonaphthalene derivatives wherein the corresponding naphthol derivative is reacted with ammonia or amines in the presence of bisulfites, the improvement which comprises carrying out the reaction in a continuous procedure in reaction apparatus which consists wholly or partly of titanium or a titanium alloy, wherein the elementary carbon content in the system used is less than 0.1% by weight.

2. Process of claim 1 wherein the reaction is carried out in reaction apparatus made of a titanium/palladium, titanium/nickel or titanium/molybdenum alloy.

3. Process of claim 1 wherein a titanium/palladium alloy with 99.0 to 99.5% by weight of titanium and 0.05 to 0.2% by weight of palladium is used.

4. Process of claim 1 wherein a titanium/nickel alloy with 97.0 to 99.5% by weight of titanium and 0.5 to 3.0% by weight of nickel is used.

5. Process of claim 1 wherein a titanium/molybdenum alloy with 50.0 to 80.0% by weight of titanium and 20.0 to 50.0% by weight of molybdenum is used.

6. Process of claim 1 wherein a titanium material which consists of 99.848% by weight of titanium, 0.03% by weight of iron, 0.01% by weight of carbon, 0.01% by weight of nitrogen, 0.1% by weight of oxygen and 0.002% by weight of hydrogen is employed.

7. Process of claim 1 wherein a titanium/palladium alloy which consists of 99.36% by weight of titanium, 0.2% by weight of palladium, 0.2% by weight of iron, 0.08% by weight of carbon, 0.05% by weight of nitrogen and 0.05% by weight of hydrogen is used.

8. Process of claim 1 wherein a multi-chamber reactor is used as the reaction apparatus.

9. Process of claim 1 wherein a multi-chamber reactor with 10 to 20 chambers is used as the reaction apparatus.

* * * * *